United States Patent [19]

Deschler et al.

[11] Patent Number: 4,704,428

[45] Date of Patent: Nov. 3, 1987

[54] SILYL SUBSTITUTED CYCLOPENTADIENE, PROCESS FOR ITS PRODUCTION AND SYNTHETIC RESIN AND RUBBER MIXTURES CONTAINING IT

[75] Inventors: Ulrich Deschler, Hanau; Peter Panster, Rodenbach; Peter Kleinschmit, Hanau; Siegfried Wolff, Bornheim-Merten; Ewe-Hong Tan, Wesseling, all of Fed. Rep. of Germany

[73] Assignee: Degussa Aktiengesellschaft, Frankfurt am Main, Fed. Rep. of Germany

[21] Appl. No.: 933,136

[22] Filed: Nov. 21, 1986

Related U.S. Application Data

[62] Division of Ser. No. 756,088, Jul. 17, 1985, Pat. No. 4,645,850.

[30] Foreign Application Priority Data

Jul. 28, 1984 [DE] Fed. Rep. of Germany ....... 3427922

[51] Int. Cl.$^4$ .............................................. C08K 3/36
[52] U.S. Cl. .................................... 524/535; 524/212; 525/288
[58] Field of Search ....................... 523/212; 524/535; 525/288

[56] References Cited

U.S. PATENT DOCUMENTS

| 4,320,214 | 3/1982 | Harayama et al. | 525/288 |
| 4,412,042 | 10/1983 | Matsuura et al. | 525/288 |
| 4,593,072 | 6/1986 | Keogh | 525/288 |

*Primary Examiner*—Lewis T. Jacobs
*Attorney, Agent, or Firm*—Cushman, Darby & Cushman

[57] ABSTRACT

The invention is directed to silylalkyl and silylaralkyl substituted cyclopentadienes which have a hydrolyzable group attached to the silicone atom, a process for their production and peroxide cross-linkable synthetic resin and rubber mixtures containing them.

17 Claims, No Drawings

SILYL SUBSTITUTED CYCLOPENTADIENE, PROCESS FOR ITS PRODUCTION AND SYNTHETIC RESIN AND RUBBER MIXTURES CONTAINING IT

This is a division of application Ser. No. 756,088, filed July 17, 1985, now U.S. Pat. No. 4,645,850, issued Feb. 24, 1984.

BACKGROUND OF THE INVENTION

The invention is directed to silyl substituted cyclopentadienes, their production and rubber and synthetic resin mixtures containing them.

Cyclopentadienyltrialkoxy silanes and cyclopentadienylalkyltrialkylsilanes are known already. The alkoxysilanes are frequently used for the production of surface coatings through hydrolysis. According to German Pat. No. 1097988 cyclopentadienyltrialkoxysilanes are obtained by reaction of the corresponding halogen compounds with an alcohol.

The starting compounds are produced previously from trichlorosilane and cyclopentadiene with a yield of less than 50% (U.S. Pat. No. 2,951,057).

It is also known to obtain cyclopentadienyltrialkoxysilanes in a direct reaction from cyclopentadiene and trialkoxysilylchlorides (U.S. Pat. No. 2,957,901).

However, after two distillations there is only obtained a moderately pure product.

In the Zh.Obshch. Khim. 1974, 44(10) (Chem. Abst. Vol. 82, item 57806q (1975) there is described a two step process for the production of 3-(triethylsilyl)propylcyclopentadiene by hydrosilylation of allyl cyclopentadiene with ethyldichlorosilane and subsequent reaction of the intermediate product in a Grignard process with ethyl bromide.

The compound obtained according to this process through the chain of methylene groups permits a greater independence from the silicon atom of reactions occurring on the cyclopentadiene ring, at the same time, however, there are no longer present hydrolyzable groups on the silicon atom.

SUMMARY OF THE INVENTION

The invention is directed to new silyl substituted cyclopentadienes of the formula:

in which A corresponds to

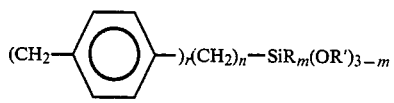

where
R and R' are the same or different and are $C_1$- to $C_6$-alkyl, $C_5$- to $C_6$-cycloalkyl, benzyl, phenyl, or substituted phenyl,
n is 1 to 3,
m is 0 or 1,
p is 1 or 2 with the proviso that when p is 2 A is the same or different and the total number of carbon atoms of the alkoxy or aryloxy groups does not exceed 36 and preferably is not over 32, and r is 0 or 1.

Compounds of the formula I in which p is 1 are produced by the reaction of a solution of cyclopentadienyl-alkali metal (e.g. sodium or potassium) in an aprotic polar organic solvent with an equimolar amount of a silane of the formula:

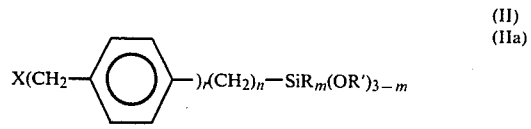

in which
R and R' are the same or different and are $C_1$ to $C_6$-alkyl, $C_5$ to $C_6$-cycloalkyl, benzyl, phenyl, substituted phenyl,
n is 1 to 3,
m is 0 or 1, r is 0 or 1,
X is Cl, Br, or I Sodium compounds of cyclopentadiene can be obtained according to the state of the art by reaction of the diene with sodium hydride.

Cyclopentadienyl potassium is obtained from cyclopentadiene and metallic potassium in benzene or xylene.

There is preferably employed a solution of sodium cyclopentadiene in tetrahydrofurane (THF).

There are also suited as solvents ethers such as diethyl ether, dibutyl ether, diphenyl ether, ethylene glycol dimethyl ether, diethylene glycol dimethyl ether as well as mixtures of the mentioned ethers with aliphatic or aromatic hydrocarbons, e.g. hexane, benzene, toluene, xylene, decane.

The reaction of the invention is carried out in the absence of water and under a protective gas, e.g. argon.

During the mixing of the silane into the solution of cyclopentadienyl-alkali, preferably sodium, in THF the temperature is controlled so that it does not exceed 35° C., since otherwise the cyclopentadiene ring will increasingly become multiple-substituted.

Subsequently the reaction solution is stirred at 20° to 65° C., preferably at room temperature, until the reaction is complete.

Depending on the halogen atom to be substituted different reaction times are needed in case of chloroalkysilanes according to formula II up to 7 days, preferably 4 days, are necessary for a complete reaction.

Corresponding iodine compounds react faster.

Subsequently the precipitate is separated from alkali halide formed via a filter, the reaction solution is freed from the employed solvent by distillation, and the desired product finally fractionated, e.g. via a Vigreux column.

The invention is further directed to a process in which the mono-silyl substituted cyclopentadiene produced as described above is slowly dosed in a aprotic polar solvent, preferably THF, at a temperature of 50° to 55° C., containing at least the equivalent amount, preferably a 1 to 1.2 times excess of NaH, based on the substitued cyclopentadiene.

Thereby the speed of dosing is regulated, via the $H_2$ development. After ending the addition stirring is continued for 1.0 to 4 hours under reflux.

Any excess NaH is separated off after cooling.

The thus prepared reaction solution is treated with a haloalkylsilane of formula II for the production of di-substituted cyclopentadienes at 0° to 150° C., preferably at room temperature, and stirred until complete reaction.

The sodium halide precipitated is filtered off, the filtrate after removing the solvent is fractionally distilled.

The desired products are isolated as a mixture of isomeric bis-silyl substituted cyclopentadiene.

Preferably there are employed as silanes according to formula II chloromethyltrimethoxysilane, chloromethyl-methyldiethoxysilane, 2-chloroethyltriethoxysilane, 2-chloroethyl-methyldiethoxysilane, 3-chloropropyl-triethoxysilane, 3-chloropropyl-methyl-diethoxysilane, (2-triethoxysilyl-ethyl)benzylchloride, (2-methyldiethoxysilylethyl)benzylchloride, the analogous bromine and iodine compounds, which just as the chloro compounds also are suited as methoxy analogues.

The invention likewise is directed to mixtures based on rubbers and synthetic resins cross-linkable to elastomers, silicate fillers and organosilicon compounds of formula I which do not contain elemental sulfur.

These types of mixtures cross-linkable with peroxide have been employed previously, above all in the cable industry, using vinyl silanes, such as e.g. vinyl-tris-2-methoxyethoxysilanes.

Because of the toxic byproducts formed during processing and because of their low flash points there have been searches for an equally good adhesive agent based on silanes which can eliminate the problems of the above mentioned vinyl silane.

It has now been found that the cyclopentadienyl derivatives of formula I can be worked into the peroxide cross-linkable mixtures in place of the vinyl silane without readjusting the existing recipes and the industrial use properties of the end products produced from these new mixtures are at least equally good and in many cases even better than the products produced using the mentioned vinyl silane.

The cyclopentadienylalkyl derivatives of formula I are present in an amount of 0.2 10 weight %, preferably up to 3.0 weight %, silicatic filler in an amount of 10 to 250 weight %, preferably 10 to 150 weight %, in each case based on 100 parts of rubber or synthetic resin.

The cross-linkable mixtures of the invention may contain the customary optional components of such mixtures such as for example anti-agers, heat stabilizers, light protective agents, ozone stabilizers, processing aids, plasticizers, adhesive agents, propellants, dyes, pigments, waxes, extenders, lead oxide, zinc oxide, and/or cross-linking activators such as triallyl isocyanurate, triallyl cyanurate or methacrylates.

In the event that in addition to the silicatic filler carbon black is present in the new mixtures the total amount of filler is reasonably limited to a maximum of 300 parts by weight based on 100 parts by weight of rubber or synthetic resin.

A process of cross-linking comprises (or consists essentially of or consists of) making a mixture containing at least one rubber or synthetic resin, at least one silicatic filler in an amount of 1 to 250 parts by weight, carbon black in an amount of 0 to 300 parts by weight, at least one peroxide known to cross-link the rubber or synthetic resin in an amount of 0.01 to 10 parts by weight and at least one organosilane of the above-stated general formula I in an amount of 0.2 to 10 parts by weight per 100 parts by weight of silicatic filler, whereby the parts by weight of the rest of the materials mentioned in each case are based on 100 parts by weight of the synthetic resin or rubber, as well as optionally further customary mixing components and heating to a temperature of 100° to 300 C. during a time between 3 and 200 minutes depending on the temperature of heating.

The cross-linking mixture of the invention advantageously additionally contains zinc oxide in an amount of 0.05 to 10 parts by weight, whereby the parts by weight in each case are based on 100 parts by weight of the rubber or synthetic resin.

As types of rubbers or synthetic resins useable in the invention there are included all rubbers and synthetic resins cross-linkable to elastomers, preferably so-called diene-elastomers.

There are included for example oil extended natural and synthetic rubbers, especially natural rubber, butadiene rubber, isoprene rubber (synthetic), butadiene-styrene rubber, butadieneacrylonitrile rubber, halogenated butyl rubber (e.g. chlorinated or brominated butyl rubber), rubber made from 2-chlorobutadiene, terpolymers made of ethylene, propylene and for example nonconjugated dienes, e.g. cyclooctadiene, norbornadiene), carboxyl rubbers, epoxide rubbers, trans-polypentamers, ethylene-vinyl acetate copolymers, ethylene-propylene copolymers as well as mixtures from the mentioned types. Especially suited are polyethylene, chlorinated polyethylene, EPDM, fluorinated rubber and mixed monomers which contain ethylene (i.e. polymers of such monomers).

In a given case there can also be included chemical derivatives of natural rubber as well as modified natural rubber for use within the scope of the invention. The silicatic fillers usable according to the invention, as well as mixtures of two or more fillers are as such known as fillers in the rubber industry. Thereby the term "silicatic filler" includes an extensive group of materials which are compatible with rubbers or can be worked in as fillers in this type of mixtures, which consist of silicates, contain silicates and respectively or contain chemically bonded silicates in the widest sense. Especially included in the silicatic fillers are highly dispersed silicas (silicon dioxide) with specific surface areas in the range of about 5 to 1,000, preferably 20 to 400 $m^2/g$ (determined with gaseous nitrogen according to the known BET method) and having primary particle sizes in the range of about 10 to 400 nm, which can be produced e.g. by precipitation from silicate solution (e.g. aqueous solution), by hydrolytic and respectively or oxidative high temperature decomposition, also called flame hydrolysis, of volatile silicon halides (e.g. silicon tetrachloride, trichloromethyl silane, dichlorodimethylsilane) or by an electric arc process. These silicas can optionally also be present as mixed oxides or oxide mixtures with the oxides of the metals aluminum, magnesium, calcium, barium, zinc, zirconium, and/or titanium.

There are also included synthetic silicates, e.g. aluminum silicate or alkaline earth silicates such as magnesium or calcium silicate with specific surface areas of about 20 to 400 $m^2/g$ and primary particle sizes of about 10 to 400 nm, naturally occuring silicates, e.g. kaolin and clay as well as naturally occuring silicas as for example quartz and kieselguhr. Glass fibers and glass fiber products such as mats, strands, fabrics, and the like as well as glass microballons are also included.

The silicate fillers mentioned are preferably employed in amounts of about 10 or in a given case somewhat below to about 250 parts by weight based on 100 parts by weight of the polymer (rubber or synthetic resin). As filler mixtures there can be mentioned silica/- kaolin or silica/glass fibers/asbestos as well as blends of the silicate containing reinforcing fillers with known rubber blacks, e.g. silica/ISAF-black or silica/glass fiber cord/HAF-black.

There are preferred as silicate fillers according to the invention the mentioned highly disperse or active silicas, especially the precipitated silicas, in amounts of 10 to 150 parts by weight, based on 100 parts of rubber or synthetic resin.

Carbon black may additionally be present in the mixtures of the invention, not only for gray or black coloration of the vulcanizate but also to produce especially valuable vulcanizate properties in which case the known rubber blacks are preferred. These valuable properties could in no way be predicted. Preferably carbon black is employed in amounts of 0 to 150 parts by weight, based on 100 parts by weight of rubber, in the new mixtures.

In the case of the presence of silicatic fillers and carbon black in the rubber mixtures the total filler content based on 100 parts by weight of rubber is limited to a maximum of 300 parts by weight, preferably up to 150 parts by weight.

Examples of radical polymerization initiators are (a) organic peroxides such as lauroyl peroxide, dipropionyl peroxide, benzoyl peroxide, di-t-butyl peroxide, t-butyl hydroperoxide and t-butylperoxy-isobutyrate, 1,3-bis(-tert.butylperoxy-isopropyl)-benzene, (b) azo compounds such as azobisisobutyronitrile and azoisobutyl valeronitrile. Besides there can be used butyl-4,4-bis-(tert.butyl peroxy)valerate, p-chlorobenzoyl peroxide, cumene hydroperoxide, tert.butyl cumyl peroxide, dicumyl peroxide, 1,1-di-tert.butyl-peroxy-3,3,5-trimethylcyclohexane (see Rubber Chemicals by J. Van Alphen, pages 133 to 139 for additional suitable initiators.

In use the described organosilane, the accelerator as well as if desired also other additives of the mixtures or several other components or one component of these mixtures, for example the filler, can be added beforehand. It is not advantageous to hydrolyze the organosilane before insertion. However, the described organosilicon compounds can suitably, especially for easier dosage and handling be mixed with a part of the silicate filler which is to be used, as a result of which the usually liquid organosilane is converted into a powdery processing product. It is also possible in a given case, however, without special advantage, to simultaneously apply the organosilane uniformly from its solution on the surface of the filler particles and to carry out the use in this form. All three or even only two of the described methods of use can also be combined.

The process for the production and shaping of the mixtures is characterized by first mixing the rubber or synthetic resin with the silicate filler (in one or more equal portions successively) in a rapidly running internal mixer in a time of 2 to 30 minutes at a rotation speed of 20 to 120 rpm and an initial temperature of 30° to 110° C., adding to this mixture the processing or plasticizer oil and the organosilane according to formula I, subsequently adding the antiaging and the UV-protectants. The compositions formed are mixed on mixing rolls at a mixing temperature of 40° to 100° C., whereby the peroxidic cross-linker is uniformly worked in within a time of 1 to 10 minutes and subsequently removed from the mixing roll apparatus.

Then the mixture is processed to molded articles at temperatures between 100° to 300° C. with the help of customary apparatuses.

Industrial areas of use for the described mixtures are the production of cable jackets, hoses, roll coverings, sealing rings, cushioning elements, etc.

The compositions can comprise, consist essentially of, or consist of the stated materials.

Unless otherwise indicated all parts and percentages are by weight.

DETAILED DESCRIPTION

Below there are given several illustrative recipes for the new mixtures with test results.

| | Measured In | Norm (German Industrial Standard) |
|---|---|---|
| Mooney-Plasticity (-viscosity) at 100° C., Normal rotor, Duration of test: 4 minutes | | DIN 53 524 |
| Tensile Strength | (MPa) | DIN 53 504 |
| Stress value at 300% Elongation (Modulus) | (MPa) | DIN 53 504 |
| Abrasion (also "DIN-Abrieb") | mm³ | DIN 53 516 |
| Compression Set B 70 h/100° C. | % | ASTM D 395 |

EXAMPLES

Production of the Compounds

In order to keep the expense low a very simple protective gas technique (flushing and filling of the glass apparatus with argon) was employed, through which the yields in the reaction were somewhat decreased.

Dicyclopentadiene was converted into the monomer (B.P. 42° C.) directly before the reaction by distillation.

NaH (remainder: paraffin oil) was employed.

Sodium cyclopentadiene (NaCp) was produced as described from cyclopentadiene (CpH) and NaH in THF.

Common Directions for the Preparation of Silanes 1–7

The red to violet colored solution of NaCp in THF was decanted from excess NaH and within 10 minutes treated with an equimolar amount of e.g. (trialkoxysilyl) alkyl chloride or (trialkoxysilyl) aralkyl chloride. The temperature thereby should not exceed 35° C. since otherwise increasingly multiple alkylation occurs. The reaction solution is stirred for 4 days at room temperature, and the formed precipitate of NaCl is separated. The reaction solution is freed from THF by distillation and finally fractionated in a vacuum via a Vigreux column.

EXAMPLE 1

(Trimethyoxysilyl)methylcyclopentadiene, 1

Production from 120 ml (1.44 mole) CpH, 55 grams (1.8 mole excess) NaH and 220 grams (1.3 mole) ClCH$_2$Si(OCH$_3$)$_3$ in 500 ml of THF.

Precipitate: 68.8 grams (91% of Th.).

Fractionation: 30 grams ClCH$_2$Si(OCH$_3$)$_3$ (B.P.$_5$=50°–60° C., 195.7 grams 1.

Yield: 75%.

Colorless liquid, B.P.$_{0.5}$=51° C.

| C$_9$H$_{16}$O$_3$Si (200,311) | C | H | Si |
|---|---|---|---|
| Calculated: | 53.97 | 8.05 | 14.02 |
| Found: | 53.33 | 8.34 | 14.00 |

EXAMPLE 2

(Trimethoxysilyl)propylcyclopentadiene, 2

Production from 90 ml (1.1 mole) (CpH, 40 grams (1.3 mole, excess) NaH and 198.6 grams (1 mole) 3—Cl—$C_3H_6$—Si(OCH$_3$)$_3$ in 500 ml THF.

Deviating from the stated directions the reaction solution after the addition of the Cl—$C_3H_6$—Si(OCH$_3$)$_3$ was refluxed for 2 hours by which procedure considerable amounts of multiple alkylation products were formed.

Precipitate: 50 grams (86% of Th.).
Fractionation: 62 grams Cl—$C_3H_6$—Si(OCH$_3$)$_3$ (B.P.$_{0.5}$=55° C.) 114.5 grams 2.
Yield: 50%.
Colorless Liquid, B.P.$_{0.5}$=85° C.

| $C_{11}H_{20}O_3Si$ (228,365) | C | H | Si |
| --- | --- | --- | --- |
| Calculated: | 57.89 | 8.77 | 12.31 |
| Found: | 57.51 | 8.96 | 12.51 |

EXAMPLE 3

(Triethoxysilyl)methylcyclopentadiene, 3

Production from 124 ml (1.5 mole) CpH, 55 g (1.8 mole, excess) NaH and 319 grams (1.5 mole) Cl—CH$_2$—Si(OC$_2$H$_5$)$_3$ in 500 ml THF.

Precipitate: 58.5 grams (67% of Th.).
Fractionation: 105.4 grams Cl—CH$_2$—Si(OC$_2$H$_5$)$_3$ (B.P.$_{.3}$=65° C.) 202.2 grams 3.
Yield: 56%.
Colorless liquid B.P.$_{10^{-2}}$=52° C.

| $C_{12}H_{22}O_3Si$ (242,392) | C | H | Si |
| --- | --- | --- | --- |
| Calculated: | 59.46 | 9.15 | 11.95 |
| Found: | 59.18 | 9.45 | 11.09 |

EXAMPLE 4

(Triethoxysilyl)propylcyclopentadiene, 4

Production from 100 ml (1.2 mole) CpH, 39 grams (1.3 mole, excess) NaH and 290 grams (1.2 mole) 3—Cl—$C_3H_6$—Si(OC$_2$H$_5$)$_3$ in 500 ml THF.

Precipitate: 55.8 grams (80% of Th.).
Fractionation: 51.5 grams Cl—$C_3H_6$—Si(OC$_2$H$_5$)$_3$ B.P.$_{0.05}$=67° C. 188.3 grams 4.
Yield: 58%.
Colorless liquid B.P.$_{0.05}$=88° C.

| $C_{14}H_{26}O_3Si$ (270,446) | C | H | Si |
| --- | --- | --- | --- |
| Calculated: | 62.18 | 9.69 | 10.38 |
| Found: | 62.10 | 9.71 | 10.60 |

EXAMPLE 5

(Tri-n-butoxysilyl)propylcyclopentadiene, 5

Production from 41.7 ml (0.5 mole) CpH, 13.2 grams (0.55 mole, excess) NaH and 162.5 grams (0.5 mole) 3—Cl—$C_3H_6$—Si(OC$_4$H$_9$)$_3$ in 250 ml THF Precipitate: 28.4 grams (97% of Th.)
Fractionation: 6.2 grams Cl—$C_3H_6$—Si(OC$_4$H$_9$)$_3$ (B.P.$_{0.04}$=99° C.) 83.3 grams 5.
Yield: 47%.

Colorless liquid, B.P.$_{0.04}$=140° C.

| $C_{20}H_{38}O_3Si$ (354,609) | C | H |
| --- | --- | --- |
| Calculated: | 67.74 | 10.80 |
| Found: | 68.30 | 11.42 |

EXAMPLE 6

(Diethoxymethylsilyl)-propylcyclopentadiene, 6

Production from 41.7 ml (0.5 mole) CpH, 13.2 grams (0.55 mole, excess) NaH and 105.4 grams (0.5 mole) 3—Cl—$C_3H_6$—Si(CH$_3$)(OC$_2$H$_5$)$_2$ in 250 ml THF.

Precipitate: 25.2 grams (90% of Th.).
Fractionation: 8.4 g Cl—$C_3H_6$—Si(CH$_3$)(OC$_2$H$_5$)$_2$ (B.P.$_{0.1}$=40° C.) 75.7 grams 6.
Yield: 63%.
Colorless liquid, B.P.$_{0.05}$=68° C.

| $C_{13}H_{24}O_2Si$ (240,420) | C | H |
| --- | --- | --- |
| Calculated: | 64.96 | 10.06 |
| Found: | 65.14 | 11.11 |

EXAMPLE 7

(Trimethoxysilyl)ethylbenzylcyclopentadiene, 7

Production from 25 ml (0.3 mole) CpH, 7.9 grams (0.33 mole, excess) NaH and 82.5 grams (0.3 mole) Cl—CH$_2$—C$_6$H$_4$—C$_2$H$_4$—Si(OCH$_3$)$_3$ in 150 ml THF Precipitate: 16.7 grams (95% of Th.).
Fractionation: 3.5 grams Cl—CH$_2$—C$_6$H$_4$—C$_2$H$_4$—Si(OCH$_3$)$_3$ (B.P.$_{0.05}$=105° C.) 33.1 grams 7.
Yield: 36.0%.
Colorless liquid, B.P.$_{0.01}$=125° C.

| $C_{17}H_{24}O_3Si$ (304,464) | C | H |
| --- | --- | --- |
| Calculated: | 67.06 | 7.95 |
| Found | 68.08 | 8.74 |

Common Directions for the Production of Silanes 8–12

A 1.2 fold excess of NaH was present in THF. There were dropped into this mixture at 50°–55° C. e.g. an equimolar amount of (trialkoxysilyl)alkylcyclopentadienes 1–4 whereby the speed of the dropping in was regulated via the H$_2$ development.

After the end of the addition of silane stirring was continued for 1 hour under reflux. After cooling it was decanted from excess NaH. Subsequently the reaction solution was treated dropwise with the corresponding haloalkyltrialkoxy silane and stirred. The reaction time was about 4 days for chloroalkylsilanes, for iodalkyl silanes, however, at most one day. The precipitated sodium halide was filtered off, the filtrate after evaporating the solvent was fractionally distilled.

EXAMPLE 8

Bis[(trimethoxysilyl)methyl]cyclopentadiene, 8

Production from 8 grams (0.26 mole, excess) NaH, 45 grams (0.22 mole) 1 and 58 grams (0.22 mole) I—CH$_2$—Si(OCH$_3$)$_3$ in 60 ml THF Precipitate: 23.5 grams (71% of Th.).
Fractionation: 21.3 grams I—CH$_2$—Si(OCH$_3$)$_3$ + 1 (B.P.$_{.4}$=35°–70° C.), 42.8 grams 8.

Yield: 58%.
Colorless liquid, B.P.$_{10^{-3}}$=95° C.

| C$_{13}$H$_{26}$O$_6$Si$_2$ (334,518) | C | H |
|---|---|---|
| Calculated: | 46.68 | 7.83 |
| Found: | 45.64 | 7.82 |

EXAMPLE 9

Bis[trimethoxysilyl)propyl]cyclopentadiene, 9

Production from 12.3 grams (0.4 mole, excess) NaH, 79.9 grams (0.35 mole) 2 and 69.3 grams (0.35 mole) 3—Cl—C$_3$H$_6$—Si—(OCH$_3$)$_3$ in 300 ml THF.

Precipitation: 16 grams (78% of Th.).

Fractionation: 12.1 grams Cl—C$_3$H$_6$—Si(OCH$_3$)$_3$ B.P.$_{0.5}$=45° C.; 3.6 grams 2 (B.P.$_{0.5}$=85° C.); 87.4 grams 9.

Yield: 64° C.
Colorless liquid B.P$_{0.01}$=145° C.

| C$_{17}$H$_{34}$O$_6$Si$_2$ (390,127); | C | H | Si |
|---|---|---|---|
| Calculated: | 52.27 | 8.77 | 14.38 |
| Found: | 52.28 | 9.26 | 13.40 |

EXAMPLE 10

Bis[(triethoxysilyl)methyl]cyclopentadiene, 10

Production according to variant A from 25 grams (0.8 mole, excess) NaH, 153 grams (0.63 mole) 3 and 108.3 grams (0.5 mole) Cl—CH$_2$—Si(OC$_2$H$_5$)$_3$ in 200 ml THF.

Precipitate: 25.5 grams (87% of Th.).

Fractionation: 13.6 grams Cl—CH$_2$—Si(OC$_2$H$_5$)$_3$ (B.P.$_1$=43° C.); 23.6 grams 3 (B.P.$_1$=50°-90° C.) 121.8 grams 10.

Yield: 58%.
Colorless liquid B.P.$_{10^{-3}}$=120° C.

| C$_{19}$H$_{38}$O$_6$Si$_2$ (418,681) | C | H |
|---|---|---|
| Calculated: | 54.51 | 9.15 |
| Found: | 55.00 | 9.25 |

EXAMPLE 11

Bis[(triethoxysilyl)propyl]cyclopentadiene, 11

Production from 12.3 grams (0.4 mole, excess) NaH, 94 grams (0.35 mole) 4 and 84.2 grams (0.35 mole) 3—Cl—C$_3$H$_6$—Si(OC$_2$H$_5$)$_3$ in 300 ml THF.

Precipitate: 17.3 grams (85% of Th.).

Fractionation: 10.4 grams Cl—C$_3$H$_6$—Si(OC$_2$H$_5$)$_3$ (B.P.$_{0.1}$=60° C.); 5.4 grams 4 (B.P.$_{0.1}$=98° C.); 108.7 grams 11.

Yield: 65%.
Colorless liquid B.P.$_{10^{-3}}$=162° C.

| C$_{23}$H$_{46}$O$_6$Si$_2$ (474,789) | C | H | Si |
|---|---|---|---|
| Calculated: | 58.19 | 9.77 | 11.83 |
| Found: | 58.09 | 9.86 | 12.09 |

EXAMPLE 12

(Trimethoxysilyl)methyl(triethoxysilyl)propylcyclopentadiene, 12

Production from 13.2 grams (0.55 mole, excess) NaH, 85.3 grams (0.5 mole) Cl—CH$_2$—Si(OCH$_3$)$_3$ and 135.1 grams (0.5 mole) 4 in 250 ml THF.

Precipitate: 21.2 grams (72% of Th.).

Fractionation: 17 grams Cl—CH—Si(OCH$_3$)$_3$ B.P.$_1$=42° C.); 21.6 grams (B.P.$_1$=110° C.; 67 grams 12.

Yield: 33%.
Colorless liquid B.P.$_{0.1}$=185° C.

USE EXAMPLES

EXAMPLE 13

The effect of cyclopentadienylpropyltriethoxysilane, a silane of the invention within formula (I) was investigated in a standard recipe based on chlorinated polyethylene.

| | (Amounts in Parts by Weight) | |
|---|---|---|
| | 1 | 2 |
| Chlorinated Polyethylene | 100 | 100 |
| Magnesium oxide | 4 | 4 |
| Finely divided, high active precipitated silica | 40 | 40 |
| Dioctyl phthalate | 12.5 | 12.5 |
| Phosphoric acid diphenyl-cresyl 12.5 | 12.5 | |
| 1,3-Bis-(tert.butyl-peroxyisopropyl(benzene) (40% active) | 6 | 6 |
| Cyclopentadienylpropyl-triethoxy silane (4) | — | 1 |
| Vulcanization temperature: 170° C. | | |
| Mooney-Viscosity, ML (1 + 4) 100° C. | 138 | 138 |
| Tensile strength (MPa) | 17.1 | 21.4 |
| Stress value at 300% (MPa) | 3.4 | 5.9 |
| DIN-Abrasion (mm$^3$) | 203 | 249 |
| Compression Set B 70/100 ° C. (%) | 54.9 | 34.1 |

It can be seen from the table that the vulcanizate containing the silane of the invention compared to the mixture without the silane had outstanding stress elongation values and Compression Set values. Thereby the viscosity was lowered which had a positive influence on the processing.

EXAMPLE 14

In a further series of experiments the effect of cyclopentadienylpropyl-triethoxysilane was investigated in clay filled EPDM mixtures.

| | 1 | 2 |
|---|---|---|
| EPDM | 100 | 100 |
| Zinc oxide | 5 | 5 |
| Clay | 100 | 100 |
| Processing oil | 25 | 25 |
| Poly-2,2,4-trimethyl-1,2-dihydroquinoline | 1 | 1 |
| 2-Mercaptobenzamidazole | 1 | 1 |
| 1,3-Bis(tert.butyl-peroxy-Isopropyl)-benzene (40% active) | 7.5 | 7.5 |
| Cyclopentadienylpropyl-triethoxysilane | — | 1 |
| Vulcanization temperature: 170° C. | | |
| Tensile strength (MPa) | 5.6 | 7.1 |
| Stress value (100%) (MPa) | 3.0 | 5.5 |
| DIN-Abrasion (mm$^3$) | 221 | 144 |
| Compression Set B 70 h/100° C. (%) | 23.1 | 9.4 |

Tensile strength, stress value, and abrasion were all considerably improved by the addition of the silane of the invention. Especially the Compression Set, which is of great importance for sealing rings, was reduced by the addition of cyclopentadienylpropyltriethoxysilane.

EXAMPLE 15

In a further experiment the action of 3 additional silanes within formula (I) was investigated in a standard recipe based on EPDM. The filler used was a finely divided, active precipitated silica (BET=40 m²/g).

|  | 1 | 2 | 3 | 4 |
|---|---|---|---|---|
| EPDM | 100 | 100 | 100 | 100 |
| Zinc oxide | 5 | 5 | 5 | 5 |
| Precipitated silica | 100 | 100 | 100 | 100 |
| Processing oil | 25 | 25 | 25 | 25 |
| Poly-2-4-trimethyl-1,2-dihydroquinoline | 1 | 1 | 1 | 1 |
| 2-Mercaptobenzimidazole | 1 | 1 | 1 | 1 |
| Cyclopentadienylpropyl-triethoxysilane | — | 0.42 | — | — |
| Bis-(trimethoxysilyl-methyl)-Cyclopentadiene | — | — | 0.62 | — |
| Bis-(trimethoxysilyl)-propyl)-cyclopentadiene | — | — | — | 0.72 |
| 1,3-Bis(tert.butyl-peroxy-isopropyl)-benzene (40%) | 7.5 | 7.5 | 7.5 | 7.5 |
| Vulcanization temperature: 170° C. |  |  |  |  |
| Tensile strength (MPa) | 3.2 | 6.9 | 5.2 | 6.4 |
| Stress value (100%) (MPa) | 2.8 | 4.8 | 4.1 | 5.2 |
| DIN-Abrasion (mm³) | 413 | 276 | 294 | 196 |
| Compression Set B 70 h/100° C. (%) | 14.3 | 7.1 | 7.1 | 5.7 |

By addition of equimolar amounts of the silanes of the invention there were greatly improved the vulcanization properties, especially tensile strength, stress value, abrasion and Compression Set.

The entire disclosure of German priority application No. P 3427922.9 is hereby incorporated by reference.

What is claimed is:

1. A mixture comprising a peroxide cross-linkable rubber or synthetic resin containing a silicate filler as a reinforcing agent and containing 0.2 to 10 parts of a silyl substituted cyclopentadiene of the formula

in which A corresponds to

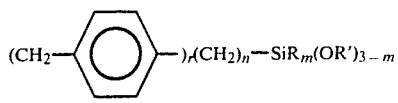

where

R and R' are the same or different and are $C_1$- to $C_6$-alkyl, $C_5$- to $C_6$-cycloalkyl, benzyl, phenyl, or substituted phenyl, n is 1 to 3, m is 0 or 1, p is 1 or 2 with the proviso that when p is 2 A is the same or different and the total number of carbon atoms of the alkoxy or aryloxy groups does not exceed 36, and r is 0 or 1 based on the silicatic filler.

2. A mixture according to claim 1 containing 0.05 to 10 parts by weight of zinc oxide, based on 100 parts by weight of the rubber or synthetic resin.

3. A mixture according to claim 1 where r is 0.

4. A mixture according to claim 2 where m is 0.

5. A mixture according to claim 4 where R' is $C_1$ to $C_6$ alkyl.

6. A mixture according to claim 5 where R' is $C_1$ to $C_3$ alkyl.

7. The product obtained by vulcanizing the mixture of claim 6 with a peroxide.

8. The product obtained by vulcanizing the mixture of claim 1 with a peroxide.

9. A process for forming a vulcanized product from the mixture of claim 1 comprising mixing in a rapidly running internal mixer for 2 to 30 minutes at 20 to 120 rpm and an initial inner mixing temperature of 30° to 110° C., the rubber or synthetic resin with the silicatic filler, mixing this mixture with the processing oil or plasticizer oil and a silyl-substituted cyclopentadiene of formula (I), subsequently adding an anti-ager and a UV protective agent and mixing the resulting composition on mixing rolls at a mixing temperature of 40° to 100° C., uniformly working in a peroxide cross-linker within 1 to 10 minutes, withdrawing the mixture from the mixing rolls and processing to a molded article at a temperature of 100° to 300° C.

10. A mixture according to claim 6 where p is 1.

11. A mixture according to claim 6 where p is 2.

12. A mixture according to claim 3 wherein m is 1.

13. A mixture according to claim 12 where R' is $C_1$ to $C_6$ alkyl.

14. A mixture according to claim 1 where r is 1.

15. A mixture according to claim 14 where R and R' are $C_1$ and $C_6$ alkyl.

16. A mixture according to claim 1 where n is 1.

17. A mixture according to claim 1 where n is 3.

* * * * *